(12) United States Patent
Barere

(10) Patent No.: US 9,164,016 B2
(45) Date of Patent: Oct. 20, 2015

(54) DEVICE FOR SAMPLING AND VAPORIZING LIQUEFIED NATURAL GAS

(75) Inventor: Pierre Barere, Enghien les Bains (FR)

(73) Assignee: OPTA PERIPH, Enghien Les Bains (FR)

( * ) Notice: Subject to any disclaimer, the term of this patent is extended or adjusted under 35 U.S.C. 154(b) by 282 days.

(21) Appl. No.: 13/993,791

(22) PCT Filed: Dec. 6, 2011

(86) PCT No.: PCT/FR2011/052884
§ 371 (c)(1),
(2), (4) Date: Jun. 18, 2013

(87) PCT Pub. No.: WO2012/080619
PCT Pub. Date: Jun. 21, 2012

(65) Prior Publication Data
US 2013/0263680 A1    Oct. 10, 2013

(30) Foreign Application Priority Data

Dec. 13, 2010 (FR) .................................... 10 60417

(51) Int. Cl.
| | |
|---|---|
| *G01N 1/44* | (2006.01) |
| *F17C 7/04* | (2006.01) |
| *F17C 9/02* | (2006.01) |
| *G01N 1/10* | (2006.01) |

(52) U.S. Cl.
CPC .. *G01N 1/44* (2013.01); *F17C 7/04* (2013.01); *F17C 9/02* (2013.01); *G01N 1/10* (2013.01)

(58) Field of Classification Search
CPC ............... F17C 7/04; F17C 9/02; G01N 1/10; G01N 1/44
See application file for complete search history.

(56) References Cited

U.S. PATENT DOCUMENTS

| | | | |
|---|---|---|---|
| 2,761,286 A * | 9/1956 | Billue et al. ................... | 62/50.2 |
| 7,337,616 B2 * | 3/2008 | Meneses et al. ............... | 62/48.1 |
| 7,484,404 B2 * | 2/2009 | Thompson et al. .......... | 73/61.59 |
| 7,882,729 B2 * | 2/2011 | Thompson et al. .......... | 73/61.57 |
| 2003/0017610 A1 | 1/2003 | Gerstel | |
| 2009/0151427 A1 | 6/2009 | Thompson | |
| 2010/0012201 A1 | 1/2010 | Welker | |

FOREIGN PATENT DOCUMENTS

| | | |
|---|---|---|
| DE | 100 56 785 A1 | 5/2002 |
| FR | 2 226 616 A2 | 11/1974 |
| FR | 2921489 A1 * | 3/2009 |
| FR | 3004257 A1 * | 10/2014 |
| WO | 2010 040940 A1 | 4/2010 |

* cited by examiner

*Primary Examiner* — John Fitzgerald
(74) *Attorney, Agent, or Firm* — Andrew W. Chu; Craft Chu PLLC

(57) ABSTRACT

The device for sampling and vaporizing liquefied natural gas includes a circuit provided at one end with a device for collecting a sample of liquefied gas and conveying the sample to a measurement device. The circuit includes and passes through a device for vaporizing the sample. The device for vaporizing includes at least one vaporization chamber having a first convergent section portion and a second divergent section portion and shaped so as to vaporize the sample under supercritical conditions at a pressure of greater than 80 bar without fractionating. The vaporization chamber includes, at the entrance of the first convergent section portion, a port with a variable opening. The port is sized so as to limit the vaporization pressure to a maximum of 90 bar in conjunction with a fixed opening at the outlet of the second divergent section portion.

4 Claims, 2 Drawing Sheets

DEVICE FOR SAMPLING AND VAPORIZING LIQUEFIED NATURAL GAS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the field of sampling liquefied natural gas (LNG).

The invention relates in particular to a sampling device.

Such a device will find a very particular application in the loading and unloading of methane carriers, the liquefaction trains, the re-condensers and any sampling device or method representative of LNG. Said device will be used for measuring the upper calorific value (by means of an in-line chromatograph or calorimeter), its Wobbe index, its composition for calculating the density of the liquid and gaseous states and for detecting eventual pollutants. In brief, the invention permits to take a sample of gas in order to check the quality and to calculate the energy in-line during the transactional transfers.

2. Description of Related Art Including Information Disclosed Under 37 CFR 1.97 and 37 CFR 1.98.

In a known way, the natural gas is condensed, for its transport, to the liquid state through a cryogenic method at a temperature in the range of −160 degrees Celsius.

Under such circumstances, heat-insulation problems arise. The known devices possess insulation means that are generally used in cryogenics. A known example of insulation consists in wrapping the sampling device in a glass-wool sheathing having a thickness of several millimeters, namely 160 mm for a K factor of 18.7 milliwatt per Kelvin-meter. Such an insulation is however not fully satisfactory.

In order to improve it, it has also been devised to exert a vacuum at the level of the sheathing of the sampling probe. Thus, putting this sheathing of the probe under vacuum permits an enhanced heat insulation, in order to reduce the risks of fractioning of the gas. Such a solution does however not completely avoid the losses due to conduction and convection. In addition, this technique does not avoid at all the losses due to radiation.

Furthermore, this degree of heat insulation is not sufficient within the framework of LNG sampling, so that it entails a risk of fractioning of the gas in the sampling line, namely because of an enthalpy absorption inducing a temperature of the sample higher than the temperature of under-cooling of the LNG. In brief, the existing devices have trouble in vaporizing the gas molecules in a complete bond, resulting into an erroneous representativity of the samplings being made and a random error beyond limits during the calculations of the upper calorific value and the densities of the liquid and gas phases based on the chromatograms being obtained.

Indeed, in the existing devices, the sampled gas is conveyed, at the outlet of the probe, through a heated coil, inside and alongside which it is suddenly vaporized. Therefore, it is not possible to accurately control the vaporization and to limit the risks of fractioning.

In addition, such a coil does not ensure a control of the change from liquid phase into gas phase of the sampling under complete vaporization conditions. A mixed phase can be present at the outlet of the coil, which also does not guarantee a complete vaporization of the sample and the performances required by the standards in force, namely EN 12838: i.e. a random error lower than 54 16.4561 Kj/Kg for the upper calorific value, $18 \times 10^{-4}$ Kg/m3 for the density of the sample in gas phase and 0.9 Kg/m3 for the density of the sample in liquid phase.

An example of an existing device for sampling and vaporizing Liquefied Natural Gas is described in US 2009/151427 and comprises a sampling probe located at an end of a circuit conveying the sampled gas to measuring means through a vaporization chamber. The gas sample taken is then evaporated directly at its inlet pressure into the vaporization chamber, without further energy transformation. This vaporization unavoidably causes a fractioning. The presence of this fractioning is explicitly shown by the presence of an accumulator capable of storing the natural gas vapors. Such an accumulator is aimed at mixing the gas vapors at the vaporization outlet with the existing and already stored gas vapors. This is a homogenization intent in order to limit the fractioning that took place during the vaporization.

Let's remind here that when a fractioning occurred there is a presence of mixed gas and liquid phases. These phases will circulate at different speeds. In particular, nitrogen and methane will evaporate first, producing gas pockets in the stream of the liquid phase. Therefore, the evaporation of the still liquid residue generates a higher measure of the other, heavier, components with intermittent bubbles of nitrogen ($N_2$) and methane ($CH_4$).

Therefore, such a device results into a non-uniformity of the measurement of nitrogen, which is one of the main pollutants looked for and the content of which must be obtained accurately. On the other hand, methane is the main component, the rate of which must also be obtained with certainty.

The accumulator thus intervenes for homogenizing the gas phases after vaporization and fractioning. However, the extreme difference between the molecular masses of the various components limits the possible homogenization of nitrogen and cannot achieve a 100% efficiency for methane. Finally, the vaporized gas sampling is unavoidably dissociated, even after passing through this accumulator.

In addition, a flow reducer is provided for, followed by releasing means, but causes a gradual pressure reduction, but weakens the liquid phase and causes the fractioning. It is then not possible to achieve a vaporization free of any fractioning.

Furthermore, the circuit passes through two check valves and is surrounded by a metallic partition without heat-insulation surrounding the explosion-proof box, inside which the heating cartridges are mounted in order to vaporize the sample. Such an arrangement unavoidably generates heat bridges upstream of the vaporization, causing an uncontrolled enthalpy absorption. These thermal losses induce a temperature of the sample higher than the temperature of the under-cooling of the LNG, causing inexorably a fractioning of the sample.

SUMMARY OF THE INVENTION

The aim of the present invention is to cope with the drawbacks of the state of the art by providing a device for sampling and vaporizing LNG ensuring a complete vaporization of the gas sampling in supercritical regime, i.e. at an initial temperature lower than −130 degrees Celsius (° C.) and at a pressure higher than 80 bar. Under these circumstances, the invention permits to control the change from liquid phase to gas phase without the presence of mixed phases inducing fractioning.

The phase transformation in supercritical regime requires maintaining sufficient pressure for the vaporization of the gas to occur in a dense phase without fractioning. In particular, for a temperature lower than −130°, the pressure is maintained at least at 80 bar at the time of the vaporization.

Thus, this step in which the liquefied natural gas passes from its liquid phase into a gas phase occurs beyond the critical point, or "circondenbar" (i.e. the organic dew point of the LNG), so as to generate a supercritical state of the gas, i.e. a state in which there is no longer any phase transition between the liquid state and the gaseous state. As far as LNG is concerned, this critical point is reached for a temperature lower than −130° C. and a pressure higher than 80 bar.

To this end, the device according to the invention provides to use the increase in volume of the gas at the time of its vaporization in order to maintain a pressure higher than 80 bars.

Such a device comprises a circuit provided at one end with the means for taking a sample of said liquefied gas and conveying said sample to measuring means, said circuit also comprising and passing through means for vaporizing said sample being taken.

It is characterized in that said vaporization means are in the form of at least one vaporization chamber comprising, successively along said circuit, a first portion with a convergent cross-section and a second portion with a divergent cross-section shaped so as to vaporize the whole of said gas sample, under supercritical conditions at a pressure higher than 80 bar generated by the vaporization and without fractioning of said sample.

It is also characterized in that said vaporization chamber comprises, at the inlet at the level of said convergent cross-section, an orifice with a varying opening, said orifice being so sized as to limit the vaporization pressure to a maximum of 90 bars in conjunction with a fixed orifice at the outlet of the divergent cross-section.

The convergent and divergent cross-sections of the invention cannot be assimilated with a flow reducer, but operate according to the principle of a venture valve. In brief, the pressure reduction does not result from a restriction caused by an orifice, but from a transformation of pressure (potential energy) into speed (kinetic energy). According to the Bernouille expression the original pressure reigning in the chamber then tends towards the saturating vapor tension of the LNG at a temperature of −130° C., i.e. 5 atmospheres. The pressure increase above the required threshold of 80 bars is then achieved due to the increase in volume of the sample during the phase transformation from the liquid state to the gaseous state, this transformation being induced by the transfer of enthalpy (namely a heat supply higher than 650 Joules).

Therefore, said transformation occurs under supercritical conditions at a pressure higher than 80 bar, permitting a chromatographic analysis of the sample that is completely free of fractioning. It should be noted that the orifice that is designed varying in the meaning of the present invention distinguishes itself in that it is designed for limiting the maximum pressure to 90 bar.

Furthermore, the device according to the invention ensures maintaining the sample in liquid phase until its vaporization point. To this end, the circuit is integrated within a casing under vacuum until the outlet of the vaporization chamber.

In this respect, according to further additional features, said sampling means are in the form of at least one probe, through which said circuit passes, enclosed in a sheathing and provided with heat-insulation means comprising means for putting said sheathing under vacuum at a pressure lower than 100 millibar.

Said insulation means preferably comprise a casing under vacuum.

In particular, said insulation means comprise a coating of said probe, said coating being formed of material made of nanotubes.

Therefore, the coil is only aimed at heating gas, which is already fully vaporized at the inlet.

This is also made possible in that the invention improves the heat-insulation of the sampling probe.

On the one hand, the probe sheathing is subjected to a negative pressure in the form of a high vacuum maintained below 100 millibar A.

On the other hand, this putting under vacuum of the sheathing is coupled with an internal insulation of this sheathing by a material structured into nanotubes.

Therefore, the low residual pressure minimizes the risks of appearing of a thermal bridge due to conduction and convection, while the insulation structured into nanotubes restricts the losses due to radiation. This combination permits to achieve an apparent heat conductivity (factor K) lower than 1 milliwatt per Kelvin-meter. Therefore, it is possible to control an enthalpy absorption smaller than the degree of undercooling and to avoid any risk of fractioning within the sampling device.

Thus, the invention permits to guarantee the performances required in compliance with the standards in force, namely EN 12838 and the above-mentioned random error restrictions.

Further features and advantages of the invention will become clear from the following detailed description of the non-restrictive embodiments of the invention, with reference to the attached figures.

DETAILED DESCRIPTION OF THE DRAWINGS

Figure 1:
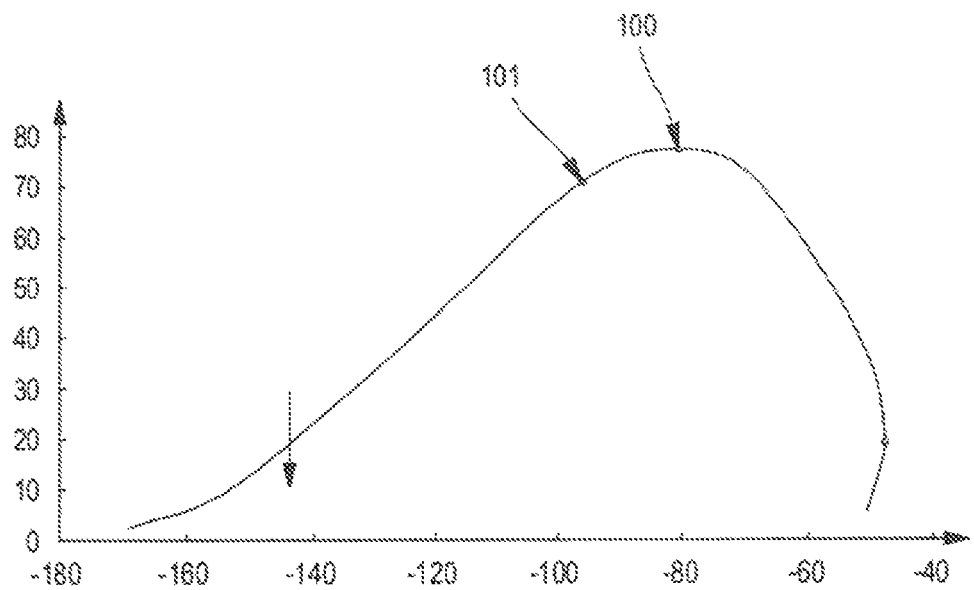
FIG. 1 represents a diagram relating to the states of transformation of the liquefied natural gas, expressing the temperature in degrees Celsius (° C.) on the abscissa axis, depending on the pressure in bar on the ordinate axis.

The invention relates to the sampling of liquefied natural gas (LNG). In particular, the invention relates to the sampling of LNG from a line, such as a duct or a pipe-line, or storage means, wherein the gas is in liquid state, in order to vaporize it and to perform qualitative and quantitative analysis on said sample having reached the gaseous state.

In particular, within its environment where it will be sampled the LNG is at a temperature of about −160° C. and a pressure of 1.5 to 18 bar.

The invention is thus aimed at taking an LNG sample under such conditions and at maintaining it under supercritical conditions during its vaporization.

To this end, the present invention relates to a device 1 for sampling and vaporizing liquefied natural gas.

Such a device 1 comprises a circuit, inside which said sample will circulate in the sampled liquid state, from its original environment, namely within a duct, to means for measuring said sample in the gaseous state after its vaporization.

In this respect, said measuring means can consist of apparatuses capable of measuring the calorific value or Wobbe index of the sample (for example, a calorimeter, a chromatograph, a spectrophotometer or another kind of analyzer), as well as its density or its composition.

Said circuit is comprised of a first section 3 and a second section 30.

First of all, the first section 3 integrates a sampling probe 4. The latter is comprised of a reinforced capillary 40, of a flange for fastening 2 said reinforced capillary 40 to the duct where the LNG is sampled and of a cryogenic valve 6 for isolating said duct, permitting the dismantling of the second section 30, for an eventual maintenance operation.

Said probe 4, the inlet of which is oriented in the direction of the flow-rate in the duct, in order to avoid any fractioning through vortex effect of the liquid phase, samples a flow-rate of the liquefied gas under the action of the pressure reigning within the duct, namely of about two liters per hour.

At the outlet of this first section 3, the reinforced capillary 40 is connected to an interface capillary 5 between the liquid and gaseous states, which can be twisted or helical. In addition, said interface capillary 5 is connected to a cryogenic valve 6. The control of this valve is performed by means of a cryogenic device formed of a long operating rod accessible after dismantling the end flange 21.

The function of this interface capillary 5 is that of avoiding the equipressure between the duct of liquefied natural gas and the gas phase that will be generated downstream.

Advantageously, said probe is provided with heat-insulation means. The latter are designed capable of maintaining a temperature within said circuit lower than 130° C.

To this end, on the one hand, said insulating means can comprise means for putting said circuit under negative pressure, at a so-called "absolute" pressure, preferably lower than 100 millibar A, namely through an electric vacuum pump or an air ejector. In particular, the insulating means are in the form of a tight sheath or casing 7 surrounding said interface capillary 5 and the inner space of which is put under high vacuum.

Therefore, this high negative pressure permits to limit an enthalpy absorption lower than the degree of under-cooling and to minimize the thermal bridges due to conduction and convection.

It should be noted that an automatically closing valve 20 can be located inside said sheathing 7 and that said valve 20 is actuated through the pilot 9 by an external device, in order to isolate the vaporizing cabinet, in case of dysfunction.

In addition, according to another feature, the inner wall of the sheathing under vacuum 7 can be sleeved by coating with an insulating material with nanotube structure.

Such a material with nanotube structure can be in the form of flexible insulating sheets made of an nano-porous aerogel. In fact, an aerogel made of silica is reinforced with microscopic, even nanoscopic, fibers ensuring a heat insulation for temperatures between −200° C. and −40° C., with a thickness smaller than one centimeter. In addition, such an insulating material is hydrophobic.

With such a coating the insulation means permit to limit the losses due to radiation at an apparent thermal conductivity (K factor) lower than 1 milliwatt per Kelvin-meter.

With such an insulation, the temperature of the sample in this portion of the circuit can be kept below −130° C., which temperature is favorable for vaporizing the sample under supercritical conditions.

The invention advantageously provides for going beyond the critical point of the LNG, so that the transformation of the LNG into the gaseous state occurs in a dense phase, without fractioning.

According to the diagram visible in FIG. 1, such conditions are met beyond the "circondenbar" point, designated by 100, well beyond the critical point, designated by 101. Below this curve of temperature depending on pressure the natural gas is in mixed—liquid and gaseous—phase. To the left and above the curve, the natural gas is in the liquid state, while it is in the fully gaseous state to the right and above said curve.

Therefore, when crossing point 100, the transition from liquid to gaseous occurs completely, without passing into a mixed phase or fractioning.

It should be noted that, according to FIG. 1, the arrow roughly shows on the curve the point of entering of the LNG sample into the vaporization means, i.e. between −160 and −130° C.

To this end, said circuit, in particular said interface capillary 5, is extended with means for vaporizing said sample being taken.

It should be noted that the temperature lower than −130° C. ensures a 100% liquid phase at the inlet of said vaporization means.

Such vaporization means are in the form of at least one vaporization chamber 11. The latter has been developed for controlling the change from liquid phase into gas of the LNG in supercritical regime, in order to guarantee complete vaporization of the sample.

At the outlet of said vaporization chamber 11 the circuit is extended with means for heating 10 the vaporized gas sample.

Figure 2:
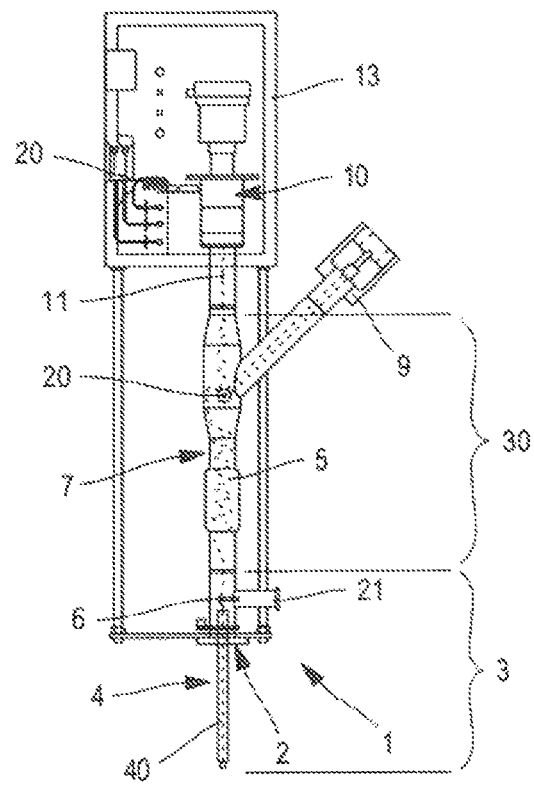
FIG. 2 is a longitudinal cross-sectional view of the whole of the device according to the invention.
Figure 3:
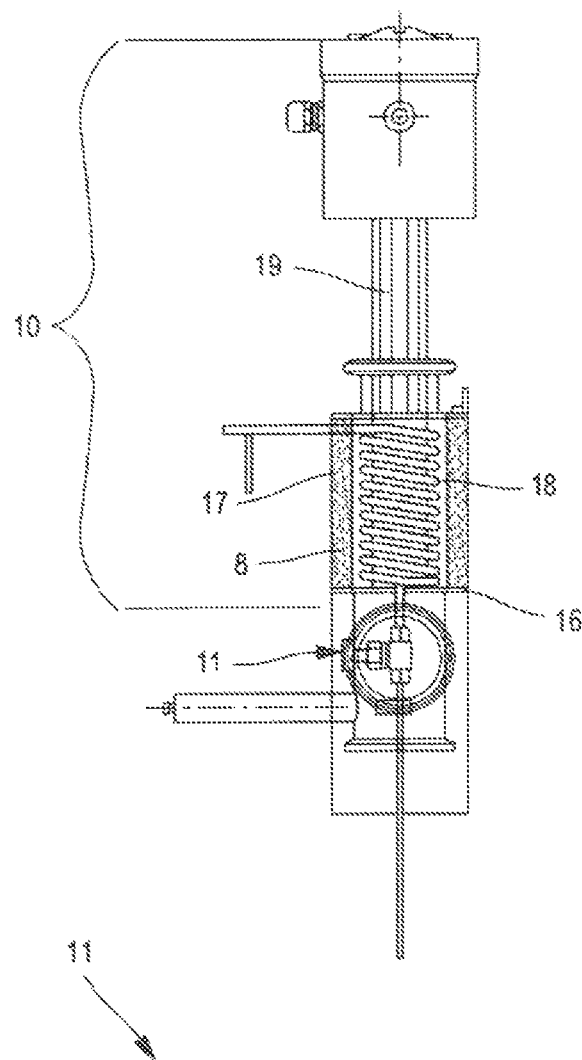
FIG. 3 is a longitudinal cross-sectional view of a detail of said device visible in FIG. 2, representing the vaporization chamber and the coil for heating the gas at the outlet of the vaporization.

As can be seen in the embodiment of FIG. 3, said heating means 10 comprise a heating coil 18, in the extension of the coil 5 visible in FIG. 2. Such a coil 18 can be formed of a tube made of metallic material, such as stainless steel. It is surrounded by adapted heating means, namely a boiler 17 filled with copper powder and incorporating electric heating resistors 19.

Such heating means permit to keep the circuit passing through them and the sample at the outlet 20 of the gas heater 10 at a positive temperature in the range of 65° C., for a temperature of the sample coming from the vaporization chamber in the range of −50° C.

In addition, said heating means are heat-insulated and can possess a room-temperature exchanger 16, so as to permit an enthalpy transfer to said vaporization chamber 11 located upstream, in order to generate the latent heat for vaporizing the sample.

In brief, this exchanger 16 provides the largest part of latent heat, which is transferred in the form of a thermal flow running along the walls of the boiler 17 and the circuit until the vaporization chamber 11.

In particular, according to a preferred embodiment, such an exchanger can be of the type exchanger with fins and possess a surface area in the range of 90 cm2.

Thus, at the inlet of the vaporization chamber 11 the temperature of the sample is at −130° C., while it reaches −50° C. at the outlet of this chamber, after changing phase, and at +65° C. at the outlet of the gas heater 10 formed by the boiler 17.

Figure 4:
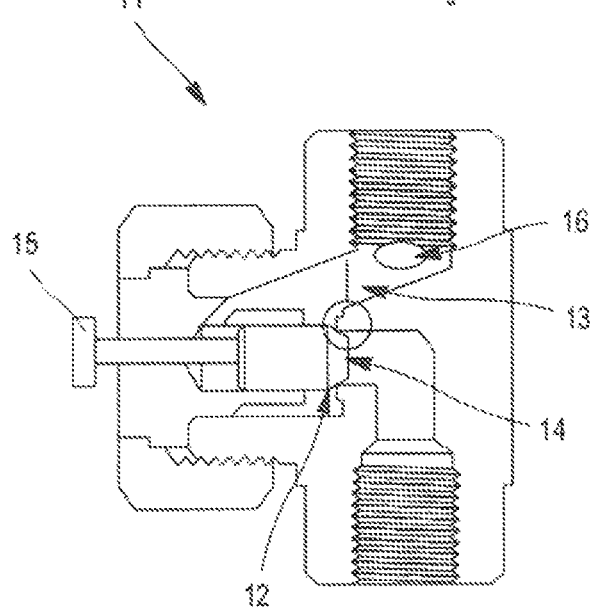
FIG. 4 represents a detail view of the vaporization chamber.

In this respect, said vaporization chamber 11, the detail of which is shown in FIG. 4, comprises successively along said circuit a first portion 12 with a convergent cross-section and a second portion 13 with a divergent cross-section. In fact, at the level of the vaporization chamber said circuit is narrowing at the level of the first portion 12 and widening at the level of the second portion 13. The vaporization chamber thus looks like a kind of "venturi".

In particular, the first 12 and second 13 portions are shaped so as to vaporize the whole of said gas sample, under supercritical conditions and without fractioning of said sample.

As evoked above, said first portion 12 is subjected at the inlet to the temperature of the sample, lower than −130° C. and, consequently, to the enthalpy transferred by said temperature exchanger 16 and the coil 5 located downstream is brought at a temperature of −50° C. corresponding to the end of the casing with mixed phase in FIG. 1.

Therefore, the conjugated effects of the release at the level of the orifice with varying opening 14, of the transformation of the potential energy into kinetic energy of the sample under the action of the convergence when it enters into the first portion 12 and of the enthalpy transfer proceeding from the heating means at the outlet of the vaporization chamber 11 bring about a complete vaporization of the gas sample.

It should be noted that without this enthalpy transfer the pressure inside the vaporization chamber would tend towards the saturating vapor tension of the LNG, i.e. about 5 atmospheres at a temperature of −130° C. The enthalpy transfer results however into a calorific supply higher than 650 Joules, exceeding the required value, i.e. the latent heat, in order to cause the complete vaporization of the sample contained in the vaporization chamber.

This transformation of the liquid phase into gaseous phase generates an increase in volume at the ratio of 1:650, increasing the pressure inside the vaporization chamber.

If the outlet of the latter were closed, the inner pressure brought about would increase up to 3250 bar, i.e. 650 times the saturating pressure. That is why at the outlet of the divergent cone of the vaporization chamber 11 is provided for a fixed opening 16 sized so as to limit the pressure to 90 bar in the vaporization chamber in conjunction with the varying orifice 14.

It should be noted then that the pressure in the whole vaporization chamber does never fall below 80 bar when the temperature of the LNG sample is below −130° C., maintaining the supercritical conditions improving the vaporization.

The invention can also provide to integrate, at the level of the inlet of the convergent section 12 of the vaporization chamber 11, an orifice 14 with varying opening, namely by means of an adjustable spring 15, in order to limit the pressure in the vaporization chamber as mentioned above, and to conjugate the transformation of liquid into gas due to the above-mentioned calorific supply with a release enhancing the vaporization of the liquid at the level of the convergent section.

It should be noted that this opening is designed adjustable, so as to manage the quantity and the flow-rate of LNG passing through said orifice 14 with varying opening, which is never completely closed.

Therefore, such an orifice with varying opening 14 ensures two functions: the limitation of the pressure and the release of the gas at the inlet of the convergent section 12, in order to initiate the vaporization process.

Furthermore, a valve with regulation of the mass flow-rate of the vaporized gas is provided for downstream of the device 1: when the temperature at the inlet of the vaporization chamber raises and exceeds the −30° C. threshold, the set value of the mass flow-rate regulator controlling this valve, of about a mean value of 1000 NI/h, is increased to 1 500 NI/h.

It should be noted that this increase in temperature can be due to a sample abnormally formed of heavier elements or to a reduction of the pressure of the initial environment, for example a line pressure lower than 2 bar.

This increase in flow-rate is maintained until the temperature is again below −130° C.

In this respect, specific means for measuring the temperature are implemented, namely a temperature-measuring probe with cryogenic extension (in order not to generate enthalpy) is mounted downstream in the close vicinity of the vaporization chamber, in order to measure the critical temperature of −130° C. foreseen at that location.

Likewise, the temperatures inside and at the outlet of the gas heater 10, as well as the electric power absorbed by the electric resistors of that very heater, are measured in order to ensure the functions of regulation, validation and safety of the whole device.

Experimental values have been obtained during the liquefaction under liquid argon of a natural gas sample, then its vaporization.

Based on these experimental measures, the enthalpy absorbed by the LNG at its sampling point to the vaporization chamber, i.e. 4462 J/kg, remains well below the permitted degree of under-cooling, i.e. at most 27000 J/kg.

Of course, the invention is not limited to the examples shown and described above, which can have variants and modifications without therefore departing from the framework of the invention.

I claim:

1. A device for sampling and vaporizing liquefied natural gas, comprising:
   a circuit comprised of:
      means for taking a sample of said liquefied gas and conveying said sample to measuring means at one end of said circuit, and
      means for vaporizing said sample, said circuit passing through said means for vaporizing, said means for vaporizing being comprised of at least one vaporization chamber with an outlet, and
      means for heating said sample, extending said circuit from said outlet,
   wherein said vaporization chamber comprises, successively along said circuit, a first portion with a convergent cross-section and a second portion with a divergent cross-section shaped so as to vaporize said sample, under supercritical conditions at a pressure higher than 80 bar generated by vaporization and without fractioning of said sample, and
   wherein said vaporization chamber comprises an inlet at a level of said convergent cross-section, and an orifice with a varying opening, said orifice being so sized as to limit vaporization pressure to a maximum of 90 bars in conjunction with a fixed orifice at an outlet of said divergent cross-section, and at said outlet of said vaporization chamber.

2. The device according to claim 1, wherein said means for taking said sample is comprised of at least one probe, enclosed in a sheathing and provided with heat-insulating means, said heat-insulating means comprising means for putting said sheathing under vacuum at a pressure lower than 100 millibar, said at least one probe passes said circuit.

3. The device according to claim 2, wherein said heat-insulating means comprises a casing under vacuum.

4. The device according to claim 2, wherein said heat-insulating means comprises a coating of said at least one probe, said coating being formed of a material comprised of nanotubes.

* * * * *